United States Patent [19]

Letchworth et al.

[11] 3,984,541
[45] Oct. 5, 1976

[54] BENZOTRIAZOLES AS STABILIZERS FOR CERTAIN INSECTICIDAL EPOXY COMPOUNDS

[75] Inventors: Peter E. Letchworth, Mountain View; Ferenc M. Pallos, Pleasant Hill, both of Calif.

[73] Assignee: Stauffer Chemical Company, Westport, Conn.

[22] Filed: Jan. 15, 1975

[21] Appl. No.: 541,293

Related U.S. Application Data

[63] Continuation of Ser. No. 390,678, Aug. 22, 1973, abandoned, which is a continuation of Ser. No. 145,560, May 20, 1971, abandoned.

[52] U.S. Cl.............................. 424/174; 424/269; 424/278
[51] Int. Cl.²........................................ A01N 9/28
[58] Field of Search................... 424/174, 278, 269

[56] References Cited
UNITED STATES PATENTS
3,701,759   10/1972   Lee et al............................ 424/278
FOREIGN PATENTS OR APPLICATIONS
1,159,137   7/1967   United Kingdom Primary Examiner—V. D. Turner
Attorney, Agent, or Firm—Edith A. Rice; Daniel C. Block

[57] ABSTRACT

The combination of insecticidal active compounds with an ultraviolet light stabilizer is described herein. The insecticidal active compounds have the following generic formula:

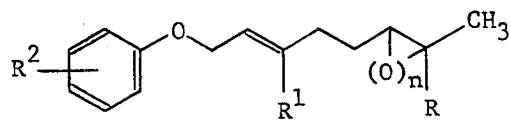

in which R and $R^1$ are independently methyl or ethyl; $n$ is the integer zero or one; $R^2$ is hydrogen, lower alkyl, lower alkenyl, lower alkoxy, halogen, nitro, lower alkylthio, or certain heterocyclic radicals. The ultraviolet stabilizers have the formula:

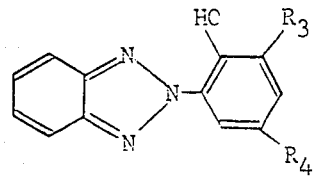

wherein $R_3$ and $R_4$ can be the same or different and can be selected from the group consisting of hydrogen, lower alkyl, lower alkoxy, lower carboalkoxy, cyclohexyl, phenyl and halogen. These stabilizers substantially enhance the useful life of the insecticidally active compounds.

9 Claims, No Drawings

BENZOTRIAZOLES AS STABILIZERS FOR CERTAIN INSECTICIDAL EPOXY COMPOUNDS

This is a division of application Ser. No. 390,678, filed Aug. 22, 1973, now abandoned which is a continuation of application Ser. No. 145,560 filed May 20, 1971, now abandoned.

DESCRIPTION OF THE INVENTION

Among the many insecticidal active compounds presently being developed, the geranyl phenyl ethers and their epoxides are notable. These compounds are represented by the following formula:

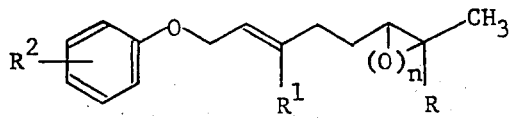

in which R and R$^1$ are independently methyl or ethyl; n is the integer zero or one; R$^2$ is hydrogen, lower alkyl, lower alkenyl, lower alkoxy, halogen, nitro, lower alkylthio, or certain hetrocyclic radicals. R can be in the cis or trans position.

This class of compounds acts in a different manner on insects than presently used insecticides and exerts a disrupting influence upon the normal development of the insects. They impede the metamorphosis of the normal pupation of the insects and result in the formation of members of the treated species which are non-viable or sterile which can ultimately lead, at least indirectly, to the destruction of the insect population. The compounds are described and claimed by Ferenc M. Pallos in copending application Ser. No. 856,140, filed Sept. 8, 1969, entitled CERTAIN GERANYL PHENYL ETHERS AND THEIR EPOXIDES AND THEIR USE IN CONTROLLING INSECTS.

In normal use, these compounds are applied to the habitat of the insects in the form of dust, spray emulsions, and the like. Thus, the compounds are exposed to heat and ultraviolet rays from sunlight. This causes degradation of the active compounds on prolonged exposure to these environmental conditions.

It has been found in practice that the useful life of the insecticidal active compounds can be substantially increased by adding thereto an effective amount of compounds generically described by the following formula:

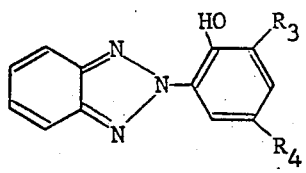

wherein R$_3$ and R$_4$ can be the same or different and can be selected from the group consisting of hydrogen, lower alkyl, lower alkoxy, lower carboalkoxy, cyclohexyl, phenyl and halogen. These compounds are described and claimed in U.S. Pat. Nos. 3,004,896 and 3,189,615 as U.V. stabilizers for plastics such as polypropylene, polyesters, polyvinyl chloride, polyethylene, acrylics, polyurethanes, polyacetals, polycarbonates and polyamides. Several of the compounds within the scope of these patents are sold under the tradename TINUVIN by Geigy Chemical Corporation of Ardsley, New York. Representative compounds are identified as 2-(2'-hydroxy-5'-methylphenyl) benzotriazole, 2-(3'-tert-butyl-2'-hydroxy-5'-methylphenyl)-5-chlorobenzotriazole and 2-(3',5'-ditert-butyl-2'-hydroxyphenyl)-5-chlorobenzotriazole.

In normal use, the amount of ultraviolet light stabilizer added thereto can range between about 0.1 and 10 percent by weight of the insecticidal active compound present.

The ultraviolet stabilizer can be admixed with the insecticidal active compounds in any conventional manner and applied to the habitat of the insect in a manner conventionally used for the dispersion of the insecticidal active compounds.

In order to illustrate the merits of the present invention, the following examples are provided:

EXAMPLES

A series of tests were conducted on the insecticidal active compound

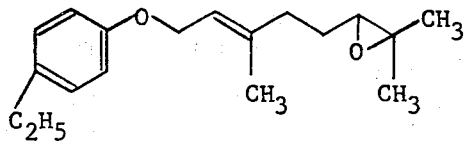

to determine the stability thereof with several different stabilizing compounds. Thus, known amounts of the insecticidal active compound were spread in a thin layer on clean glass slides. The slides were then exposed to a total of 24 hours of sunlight. Exposures were made for eight hours on three consecutive days. Following exposure, the active compound was rinsed from the slide with acetone, diluted appropriately and topically applied to Tenebrio pupae as follows:

The degree of activity of a candidate compound to hinder or impede the metamorphosis of insects is measured by treating the penultimate larval stage of a representative insect with the composition and examining it after its last molt toward the adult form for retention of immature features.

Specifically, yellow mealworm, Tenebrio molitor, L., larvae are maintained at 28° C. and 40% humidity on a diet of bran flakes. Prepupae are collected from the culture and kept in separate containers. The pupae, collected once daily, are 1–25 hours old at the time of treatment. By means of a syringe, suitable amounts of candidate compounds in 0.5 or 1.0 µl of acetone are applied to the venter of Tenebrio molitor, L. pupae. Treated pupae are maintained at 28° C. and 40% humidity until the adults emerged (usually within 6–8 days). Emerged adults are graded as positive, negative, or dead. To be considered a positive response, the presence of typical pupal cuticle, urogomphi, gin trap, and abnormal wings, etc. are required. For each test, 2 groups of 20 pupae were used and the averaged results were reported.

The dose of a candidate composition per pupa that is needed to kill or give a positive response in the above insecticidal evaluation test for 10 of the 20 pupae is determined. Table I shows these doses under the column ED$_{50}$.

The compositions of this invention are generally embodied into a form suitable for convenient application. For example, the compositions can be embodied into pesticidal formulations which are provided in the form of emulsions, suspensions, solutions, dusts, and aerosol sprays. In general, such formulations will contain, in addition to the active compound, the adjuvants which are found normally in pesticide preparations. In these formulations, the active compounds of this invention can be employed as the sole pesticide component or they can be used in admixture with other compounds having similar utility. The pesticide formulations of this invention can contain, as adjuvants, organic solvents, such as sesame oil, xylene range solvents, heavy petroleum, etc.; water; emulsifying agents; surface active agents; talc; pyrophyllite; diatomite; gypsum; clays; propellants, such as dichlorodifluoromethane, etc. If desired, however, the active compositions can be applied directly to feedstuffs, seeds, etc. upon which the pests feed. When applied in such a manner, it will be advantageous to use a composition which is not volatile. In connection with the activity of the presently disclosed pesticidal compositions, it should be fully understood that it is not necessary that they be active as such. The purposes of this invention will be fully served if the composition is rendered active by external influences, such as light, or by some physiological action which occurs when the compound is ingested into the body of the pest.

The precise manner in which the pesticidal compositions of this invention are used in any particular instance will be readily apparent to a person skilled in the art. Generally, the active pesticide composition will be embodied in the form of a liquid composition; for example, an emulsion, suspension, or aerosol spray. While the concentration of the active pesticide composition in the present formulation can vary within rather wide limits, ordinarily the pesticide composition will comprise not more than about 50.0% by weight of the formulation.

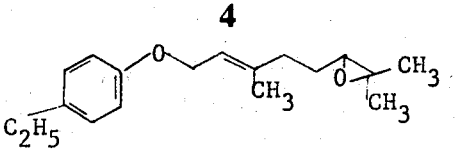

b. a stabilizing amount of a stabilizer corresponding to the formula:

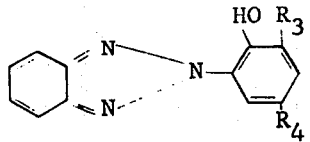

wherein $R_3$ and $R_4$ can be the same or different and can be selected from the group consisting of hydrogen, lower alkyl, lower alkoxy, lower carboalkoxy, cyclohexyl, phenyl and halogen.

2. The composition as set forth in claim 1 wherein said stabilizer is present in an amount ranging between about 0.1 and 10 percent by weight of the compound.

3. The composition as set forth in claim 1 wherein said stabilizer is 2-(2'-hydroxy-5'methylphenyl) benzotriazole.

4. The composition as set forth in claim 1 wherein said stabilizer is 2-(3'-tert-butyl-2'-hydroxy-5'-methylphenyl)-5-chlorobenzotriazole.

5. The composition as set forth in claim 1 wherein said stabilizer is 2-(3',5'-ditert-butyl-2'-hydroxyphenyl)-5-chlorobenzotriazole.

6. The composition as set forth in claim 1 further containing an inert adjuvant.

7. The composition as set forth in claim 2 further containing an inert adjuvant.

TABLE I

| Run No. | Amount of Active Compound % by Wt. | Stabilizer | Amount of Stabilizer % by Wt. | ED-50 μg /pupa Unexposed | Exposed |
|---|---|---|---|---|---|
| 1 | 100 | — | — | 0.002 | 0.01 |
| 2 | 95 | TINUVIN P | 5 | 0.002 | 0.002 |
| 3 | 97 | tetrakis[methylene 3-(3',-5'-di-t-butyl-4'-hydroxyphenyl)propionate]methane* | 3 | 0.002 | 0.04 |
| 4 | 97 | octadecyl 3-(3',5'-di-tert-butyl-4'-hydroxyphenyl)propionate** | 3 | 0.003 | 0.02 |
| 5 | 92 | 5% by wt. TINUVIN 328 with 3% by wt. conventional alkylated phenol antioxidant stabilizer | 8 | 0.002 | 0.003 |

*Sold under tradename Irgonox 1010 by Geigy Chemical Corp. of Ardsley, N.Y. as an antioxidant and thermal stabilizer.
**Sold under tradename Irgonox 1076 by Geigy Chemical Corp. of Ardsley, N.Y. as an antioxidant and thermal stabilizer.

What is claimed is:
1. A stabilized insecticidal composition consisting of:
 a. an effective amount of an insecticidal active compound having the formula:

8. The composition as set forth in claim 4 further containing an inert adjuvant.

9. The composition as set forth in claim 5 further containing an inert adjuvant.